United States Patent
Karrer

[11] 4,007,280
[45] Feb. 8, 1977

[54] 1,4-BENZODIOXAN DERIVATIVES AND PESTICIDAL USE THEREOF

[75] Inventor: Friedrich Karrer, Basel, Switzerland

[73] Assignee: Ciba-Geigy Corporation, Ardsley, N.Y.

[22] Filed: June 16, 1975

[21] Appl. No.: 587,446

[30] Foreign Application Priority Data

June 21, 1974 Switzerland .......... 8542/74
Feb. 25, 1975 Switzerland .......... 2375/75
May 29, 1975 Switzerland .......... 6945/75

[52] U.S. Cl. .................. 424/278; 260/340.3
[51] Int. Cl.² ............. A01N 9/28; C07D 319/20
[58] Field of Search ........... 260/340.3; 424/278

[56] References Cited
UNITED STATES PATENTS 3,819,655  6/1974  Chodnekar et al. ........ 260/340.3
3,910,892  10/1975 Chodnekar et al. ........ 260/340.3

*Primary Examiner*—V. D. Turner
*Attorney, Agent, or Firm*—Harry Falber

[57] ABSTRACT

The invention provides new 2-phenoxymethylene-1,4-benzodioxan derivatives of the formula

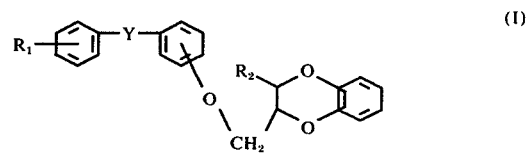
(I)

wherein $R_1$ represents alkyl of 1 to 3 carbon atoms or chlorine, $R_2$ represents hydrogen, alkyl of 1 to 3 carbon atoms and Y represents —O—, —CH$_2$—, —S— or >C=O, a process for their manufacture, pesticidal compositions containing them and a method of combatting insects by using these compounds.

15 Claims, No Drawings

1,4-BENZODIOXAN DERIVATIVES AND PESTICIDAL USE THEREOF

The present invention provides 2-phenoxymethylene-1,4-benzodioxan derivatives, a process for their manufacture and a method of using them in pest control.

The 2-phenoxymethylene-1,4-benzodioxan derivatives have the formula

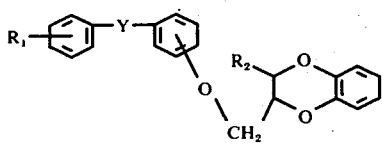

wherein $R_1$ represents alkyl of 1 to 3 carbon atoms or chlorine, $R_2$ represents hydrogen, alkyl of 1 to 3 carbon atoms and Y represents —O—, —CH$_2$—, —S— or >C=O.

Preferred compounds on account of their action are those of the formula (I) wherein $R_1$ represents hydrogen, methyl or chlorine, $R_2$ represents hydrogen and Y represents —O—, —CH$_2$— or —S—.

The most preferred compounds are those of the formula (I) wherein $R_1$ and $R_2$ represents hydrogen and Y represents —O—, —CH$_2$— or —S—.

The compounds according to the invention are manufactured by methods which are known per se, for example in the following manner:

Compounds of the formula I are suitable for combating a variety of animal and plant pests. They are therefore suitable for combating acarides, but are used especially for combating insects of the following families: acrididae, blattidae, gryllidae, gryllotalpidae, tettigoniidae, cimicidae, pyrrhocoridae, reduviidae, aphidae, delphacidae, dispididae, pseudococcidae chrysomelidae, coccinellidae, bruchidae, scarabaeidae, dermestidae, tenebrionidae, bostrichidae, cucujidae, curculionidae, tineidae, noctuidae, lymantridae, pyralidae, galleridae, culicidae, tipulidae, stomoxydae, muscidae, calliphoridae, trypetidae and pulicidae.

The insecticidal or acaricidal action can be substantially broadened and adapted to given circumstances by addition of other insecticides and/or acaricides. Examples of suitable additives are: organic phosphorus compounds, nitrophenols and derivatives, ureas, carbamates, chlorinated hydrocarbons, or pyethroids.

The compounds of the formula I may be used as pure active substance or together with suitable carriers and/or additives. Suitable carriers and additives can be solid or liquid and correspond to the substances conventionally used in formulation technology, for example natural or regenerated substances, solvents, dispersants, wetting agents, stickers, thickeners, binders and/or fertilisers.

For application, the compounds of the formula I may be processed to dusts, emulsion concentrates, granules, dispersions, sprays, to solutions, or suspensions, in the

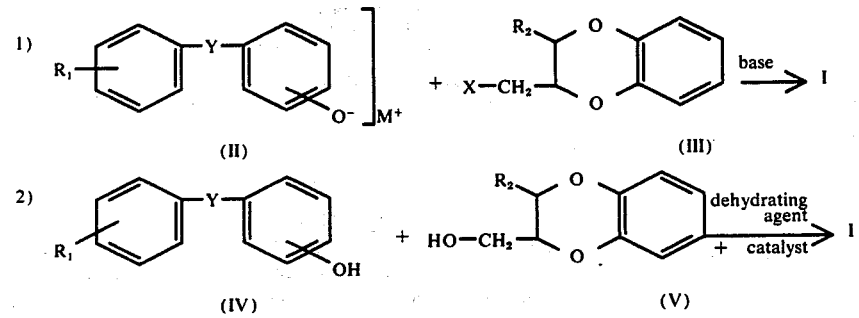

$R_1$, $R_2$ and Y in the formulae II to V have the meanings previously assigned to them for formula (I), X represents a halogen atom, especially chlorine, bromine or iodine, and M represents a metal of the 1st. or 2nd. main group of the Periodic Table, in particular sodium or potassium.

Suitable dehydrating agents are, for example, N,N-substituted carbodiimides, in particular N,N-dicyclohexyl-carbodiimide, and a suitable catalyst is e.g. copper (I) chloride. Processes 1 and 2 are carried out at a reaction temperature between +10° and 150° C, preferably at +50° to 130° C, at normal pressure and, if appropriate, in the presence of inert solvents or diluents.

Examples of suitable solvents or diluents for method 1) are ethers, e.g. 1,2-dimethoxyethane, dioxan, tetrahydrofuran; N,N-dialkylated carboxy amides, e.g. dimethyl formamide; ketones, e.g. acetone, methyl ethyl ketone or cyclohexanone; also hexamethylphosphoric triamide, dimethyl sulphoxide. The starting materials of the formulae II to V are known compounds or compounds which can be manufactured in analogous manner to known methods which are described in the literature.

conventional formulation which is commonly employed in application technology.

The compositions according to the invention are manufactured in known manner by intimately mixing and/or grinding active substances of the formula I with the suitable carriers, optionally with the addition of dispersants or solvents which are inert to the active substances.

The active substances may take, and be used in, the following forms: Solid forms:

Dusts, tracking agents, granules, coated granules, impregnated granules and homogeneous granules. Liquid forms:

a. active substances which are dispersible in water: wettable powders, pastes, emulsions;

b. solutions.

The content of active substance in the above described compositions is between 0.1 to 95%.

The active substances of the formula I can, for example, be formulated as follows:

Dusts

The following substances are used to manufacture a) a 5% and b) a 2% dust:

| | | |
|---|---|---|
| a) | 5 | parts of active substance |
| | 95 | parts of talcum |
| b) | 2 | parts of active substance |
| | 1 | part of highly disperse silicic acid |
| | 97 | parts of talcum. |

The active substances are mixed with the carriers and ground.

Granules

The following substances are used to produce 5% granules:

| | |
|---|---|
| 5 | parts of active substance, |
| 0.25 | parts of epichlorohydrin, |
| 0.25 | parts of cetyl polyglycol ether, |
| 3.50 | parts of polyethylene glycol, |
| 91 | parts of kaolin (particle size 0.3 - 0.8 mm). |

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.

Wettable powder

The following constituents are used for the preparation of a) a 40%, b) and c) a 25%, and d) a 10% wettable powder:

| | | |
|---|---|---|
| a) | 40 | parts of active substance, |
| | 5 | parts of sodium lignin sulphonate, |
| | 1 | part of sodium dibutyl-naphthalene sulphonate, |
| | 54 | parts of silicic acid. |
| b) | 25 | parts of active substance, |
| | 4.5 | parts of calcium lignin sulphonate, |
| | 1.9 | parts of Champagne chalk/hydroxyethyl cellulose mixture (1:1), |
| | 1.5 | parts of sodium dibutyl naphthalene sulphonate, |
| | 19.5 | parts of silicic acid, |
| | 19.5 | parts of Champagne chalk, |
| | 28.1 | parts of kaolin. |
| c) | 25 | parts of active substance, |
| | 2.5 | parts of isooctylphenoxy-polyoxyethylene-ethanol, |
| | 1.7 | parts of Champagne chalk/hydroxyethyl cellulose mixture (1:1), |
| | 8.3 | parts of sodium aluminium silicate, |
| | 16.5 | parts of kieselgur |
| | 46 | parts of kaolin. |
| d) | 10 | parts of active substance, |
| | 3 | parts of a mixture of the sodium salts of saturated fatty alcohol sulphates, |
| | 5 | parts of naphthalenesulphonic acid/formaldehyde condensate, |
| | 82 | parts of kaolin. |

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce a) a 10%, b) a 25% and c) a 50% emulsifiable concentrate:

| | | |
|---|---|---|
| a) | 10 | parts of active substance, |
| | 3.4 | parts of epoxidised vegetable oil, |
| | 13.4 | parts of a combination emulsifier consisting of fatty alcohol polyglycol ether and alkyl aryl sulphonate calcium salt, |
| | 40 | parts of dimethylformamide, |
| | 43.2 | parts of xylene, |
| b) | 25 | parts of active substance, |
| | 2.5 | parts of epoxidised vegetable oil, |
| | 10 | parts of an alkylarylsulphonate/fatty alcohol-glycol ether mixture, |
| | 5 | parts of dimethylformamide, |
| | 57.5 | parts of xylene. |
| c) | 50 | parts of active substance, |
| | 4.2 | parts of tributylphenol polyglycol ether, |
| | 5.8 | parts of calcium dodecylbenzenesulphonate, |
| | 20 | parts of cyclohexanone, |
| | 20 | parts of xylene. |

From these concentrates it is possible to produce by dilution with water, emulsions of any desired concentration.

Spray

The following constituents are used to prepared a) a 5% and b) a 95% spray:

| | | |
|---|---|---|
| a) | 5 | parts of active substance, |
| | 1 | part of epichlorohydrin, |
| | 94 | parts of benzene (boiling limits 160° C–190° C). |
| b) | 95 | parts of active substance, |
| | 5 | parts of epichlorohydrin. |

EXAMPLE 1

A mixture of 18.6 g of 4-phenoxyphenol, 20.7 g of 2-hydroxymethyl-1,4-benzodioxan, 22.9 g of N,N'-dicyclohexylcarbodiimide and 0.03 g of copper (I) chloride is heated for 48 hours to 105°–110° C in the process of which a melt forms. The reaction mixture is then cooled to room temperature and treated with 300 ml of diethyl ether. The copper (I) chloride and precipitated N,N'-dicyclohexyl urea are filtered off and the filtrate is washed repeatedly with 10% potassium hydroxide solution and then with water and saturated saline solution. The ethereal solution is dried over sodium sulphate and the ether distilled off. The residue is further purified by chromatography on silica gel (eluant: diethyl ether/hexane 1:4) to yield pure 2-(4-phenoxy)-phenoxymethylene-1,4-benzodioxan of melting point 73°–74° C (compound 1).

The following compounds can also be manufactured in analogous manner:

| Compound No. | | |
|---|---|---|
| 2 | 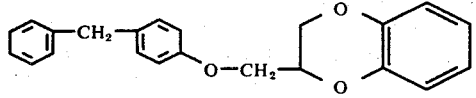 | m.p. 46°–47° C |

-continued

| No. | Structure | Property |
|---|---|---|
| 3 | C₆H₅—S—C₆H₄—O—CH₂—(1,3-dioxan-2-yl fused benzene) | $n_D^{20}: > 1.71$ |
| 4 | C₆H₅—O—C₆H₄—O—CH₂—(benzodioxane) | m.p. 64°–65° C |
| 5 | (3-methylphenyl)—O—C₆H₄—O—CH₂—(benzodioxane) | m.p. 67°–68° C |
| 6 | H₃C—C₆H₄—O—C₆H₄—O—CH₂—(benzodioxane) | m.p. 79°–80° C |
| 7 | Cl—C₆H₄—O—C₆H₄—O—CH₂—(benzodioxane) | m.p. 66°–67° C |
| 8 | C₆H₅—O—C₆H₄—O—CH₂—CH(CH₃)—(benzodioxane) | m.p. 61°–63° C |
| 9 | C₆H₅—C(=O)—C₆H₄—O—CH₂—(benzodioxane) | m.p. 75°–76° C |

EXAMPLE 2

A. Contact action on dysdercus fasciatus larvae

A given amount of a 0.1% solution of active substance in acetone (corresponding to 10 mg of active substance/m²) was pipetted into an aluminium dish and evenly distributed. After the acetone had evaporated, 10 dysdercus fasciatus larvae in the 5th. stage were put into the treated dish which contained feed and moist cotton wool. The dish was then covered with a screen top. After about 10 days, i.e. as soon as the controls had fully shed and emerged to the adult stage, the test subjects were examined for the number of adults.

Compounds according to Example 1 acted well in this test.

B. Contact action on aedes aegypti larvae

Approximately 20 two-day old larvae of the yellow fever fly (aedes aegypti) are put into a beaker containing a solution of the active substance (concentration 5 ppm). After the controls had shed and emerged to the adult stage, the test subjects were examined and the percentage of normal adults in comparison to the controls was determined.

Compounds according to Example 1 acted well in this test.

C. Contact action on Tenebrio molitor pupae

A given amount of a 0.1% solution of active substance in acetone (corresponding to 10 mg of active substance/m²) was pipetted into an aluminium dish and evenly distributed. After the acetone had evaporated, 10 freshly shed pupae were laid on the treated surface. The dish was covered with a screen top. After the controls had emerged from the cocoon as imagines, the test subjects were examined for the number of normal adults.

Compounds according to Example 1 acted well in this test.

EXAMPLE 3

50 g of wheat flour were mixed in two beakers with a given amount of active substance formulated as a 5% dust to give a concentration of 0.05%. Then 10 Ephestia kuhniella larvae were added per beaker (25 g of flour). The development of the population was recorded over the course of 8 weeks and the number of moths determined.

Compounds according to Example 1 acted well in this test against Ephestia kuhniella.

EXAMPLE 4

Action against storage pests

Wheat was treated with the active substance (10 ppm) and populated with 25 adult beetles at a time. After an exposure time of 3 months, the number of test subjects compared with the untreated controls was determined.

The compounds according to Example I acted very well against *Trogoderma granarium*, *Sitophilus granarius*, *Rhyzoptera dominica*, *Tribolium castaneum* and *Oryzaephilus surinamensis*.

I claim:
1. A compound of the formula

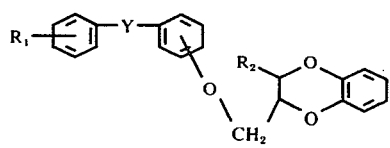
(I)

wherein $R_1$ represents hydrogen, alkyl of 1 to 3 carbon atoms or chlorine, $R_2$ represents hydrogen or alkyl of 1 to 3 carbon atoms, and Y represents —O—, —CH$_2$—, —S— or >C=O.

2. A compound according to claim 1, wherein $R_1$ represents hydrogen, methyl or chlorine, $R_2$ represents hydrogen, and Y represents —O—, —CH$_2$— or —S—.

3. A compound according to claim 1, wherein $R_1$ represents hydrogen, $R_2$ represents hydrogen, and Y represents —O—, —CH$_2$— or S.

4. A compound according to claim 3 of the formula

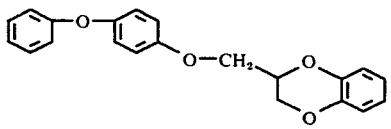

5. A compound according to claim 3 of the formula

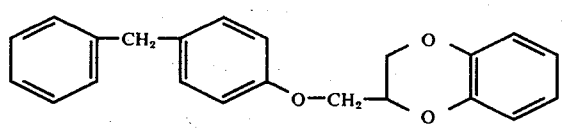

6. A compound according to claim 3 of the formula

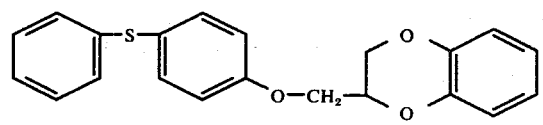

7. A compound according to claim 3 of the formula

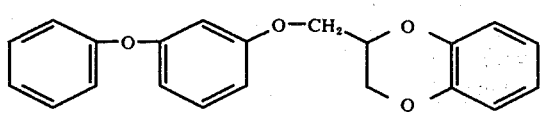

8. A compound according to claim 2 of the formula

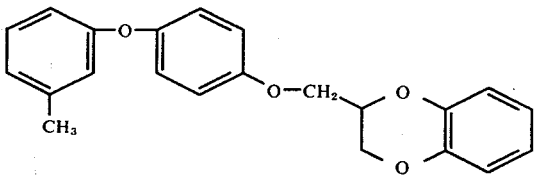

9. A compound according to claim 2 of the formula

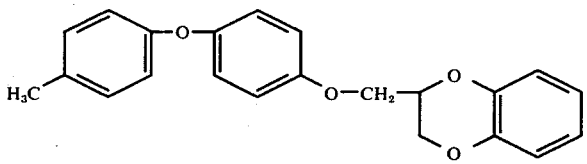

10. A compound according to claim 2 of the formula

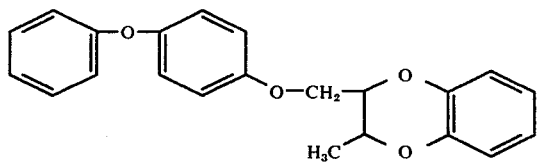

11. A compound according to claim 1 of the formula

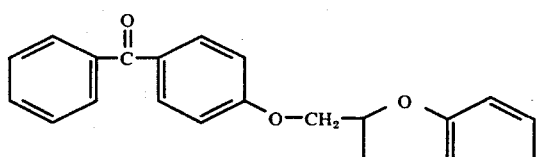

12. A compound according to claim 1 of the formula

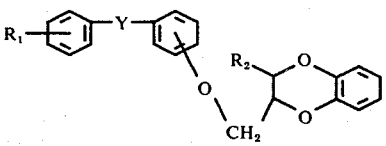

13. An insecticidal and acaricidal composition which contains as active component an insecticidally and acaricidally effective amount of a compound of the formula (I)

wherein R₁ represents hydrogen, alkyl of 1 to 3 carbon atoms or chlorine, R₂ represents hydrogen or alkyl of 1 to 3 carbon atoms, and Y represents —O—, —CH₂—, —S— or >C=O, together with a suitable carrier therefor.

14. A composition according to claim 13 which contains as active component a compound of claim 2.

15. A method of combatting insects and acarids which comprises applying to the said insects and acarids or the locus thereof an insecticidally and acaricidally effective amount of a compound of the formula

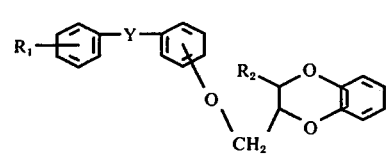

wherein R₁ represents alkyl of 1 to 3 carbon atoms or chlorine, R₂ represents hydrogen or alkyl of 1 to 3 carbon atoms and Y represents —O—, —CH₂—, —S— or >C=O.

* * * * *